United States Patent [19]

Jackson et al.

[11] 4,377,880

[45] Mar. 29, 1983

[54] CLEANING METHOD AND APPARATUS

[75] Inventors: Darryl D. Jackson; Robert M. Hollen, both of Los Alamos, N. Mex.

[73] Assignee: The United States of America as represented by the United States Department of Energy, Washington, D.C.

[21] Appl. No.: 239,228

[22] Filed: Feb. 27, 1981

[51] Int. Cl.$^3$ .............................................. A47L 5/38
[52] U.S. Cl. ...................................... 15/302; 15/304; 73/864.24; 134/147; 134/174; 134/184
[58] Field of Search .................. 15/302, 304; 134/147, 134/174, 184; 73/864.24

[56] References Cited

U.S. PATENT DOCUMENTS

1,854,471  4/1932  Hofmann .......................... 15/304 X
2,437,968  3/1948  Palotsee .......................... 134/147 X
2,814,575  11/1957  Lange ............................... 15/302 X
3,081,158  3/1963  Winter ......................... 73/864.24 X Primary Examiner—Chris K. Moore
Attorney, Agent, or Firm—Elizabeth O. Slade; Paul D. Gaetjens; Richard G. Besha

[57] ABSTRACT

A new automatable cleaning apparatus which makes use of a method of very thoroughly and quickly cleaning a gauze electrode used in chemical analyses is given. The method generates very little waste solution, and this is very important in analyzing radioactive materials, especially in aqueous solutions. The cleaning apparatus can be used in a larger, fully automated controlled potential coulometric apparatus. About 99.98% of a 5 mg. plutonium sample was removed in less than 3 minutes, using only about 60 ml. of rinse solution and two main rinse steps.

9 Claims, 9 Drawing Figures

CLEANING METHOD AND APPARATUS

BACKGROUND OF THE INVENTION

The present invention relates generally to a method of very effectively cleaning and to an automated apparatus for performing such cleaning and relates more particularly to a method for cleaning radioactive materials from electrolysis cells and electrodes and relates to the automated apparatus for performing that cleaning. The invention is a result of a contract with the Department of Energy (Contract No. W-7405-ENG-36).

In running chemical analyses on materials containing radioactive elements, an important problem is how to clean the electrodes and sample cells and other cell contents very thoroughly without generating a lot of waste solution. This is an especially difficult problem when the electrode used is a gauze electrode because the gauze tends to retain liquid. In order to decrease the time required for analysis of a sample, a gauze electrode is very useful (especially in controlled potential coulometric analyses) because it has a large surface area. However, that large surface area needs to be cleaned after each run; and using such an electrode thus brings in problems which must then be solved. Additionally, if the cleaning is to be done by an automated instrument, the steps of automating also generally tend to produce large amounts of waste solution.

Automated attempts by others to clean such gauze electrodes have included using a fixed aspirator tip which is placed at or near the bottom of the container which contains the material being analyzed. However, this approach has the disadvantage that some liquid often remains in the electrode because the electrode does not thoroughly drain on its own, much like a window screen retains water after it has been rinsed. Additionally, the fixed aspirator tip during runs will be partially filled with some of the sample being analyzed; and if the sample is quite concentrated as is often the situation when analyses are being done, upon adding diluent to the sample prior to analysis, one will not obtain an accurate reading due to the amount that remains within the aspiration tip.

In conjunction with the fixed aspirator tip, the attempts of others at cleaning the gauze electrode have included using single or multiple spray heads and spraying the electrode, followed by aspiration of the waste liquid. In order to prevent shadows from occurring, one must use multiple spray heads in this procedure. However, the use of one or more spray heads has the disadvantages that splashing often occurs and much waste solution is generated. The generation of large amounts of waste solutions is very undesirable when dealing with radioactive materials because handling problems are increased as the volume of waste increases; and when aqueous solutions are involved, attempts to evaporate off the water do not give good solutions to the problem.

Another approach used in conjunction with the fixed aspirator tip described above has been to fill up the container with rinse solution a large number of times, and to aspirate between fillings. This solution, however, also generates much waste solution and therefore is undesirable.

Other solutions have included attempting to clean only the gauze electrode automatically (and to clean the container cells manually) by filling only every other position with sample and filling the remaining cells with rinse solution. Some have used aspiration, whereas others have not. However, cleaning is not very effective in this approach and only half of the cells are used as sample cells.

When using the approaches described above, often a magnetic stirrer has been used in order to aid in the rinsing of the gauze electrode. However, this stirring presents problems, particularly if the gauze electrode is situated on the bottom of the container. Furthermore, the noise created by the magnetic stirrer affects the electrical measurements made in controlled potential coulometry methods.

Despite the prior art solutions to the problem of cleaning a gauze electrode described above, a need still exists for a method and apparatus for thoroughly cleaning a gauze electrode without generating much waste solution. This is a very serious and important problem wherever and whenever radioactive materials are analyzed.

SUMMARY OF THE INVENTION

An object of this invention is an apparatus for cleaning a gauze electrode very efficiently and thoroughly, using less time and generating less waste solution than has been possible in other apparatuses which have been used.

Yet another object of this invention is an apparatus which is automated and which will carry out a very efficient and fast rinsing operation, so as to result in very accurate sample readings without generation of much waste solution.

A still further object of this invention is an automated instrument which will remove at least 99.9% of all plutonium from a beaker, a gauze electrode and other cell contents in two rinses.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, the method of this invention comprises:

quickly and thoroughly removing all visible liquid from a gauze electrode located within a container and from the container and its other contents by: (a) positioning an aspirator tip at a single position located at the junction of the lowest extremity of the gauze electrode and the bottom of the container and then (b) aspirating.

In a preferred embodiment, the method comprises:

very thoroughly cleaning a beaker and a gauze electrode used (for example) in radioactive sample analyses by: (a) withdrawing the solution which was analyzed by means of an aspiration tip which is precisely positioned at the junction between the bottom of the gauze electrode and the bottom of the beaker; (b) then removing the aspiration tip; (c) with the gauze electrode remaining at its stationary position on the bottom of the beaker, adding rinse solution by means of a small tube (as opposed to by spraying); (d) stirring, in the presence of the gauze electrode; (e) reinserting the aspiration tip to its precise position (at the junction between the bottom of the gauze electrode and the bottom of the beaker); (f) then aspirating; (g) then removing the aspiration tip; and (h) then repeating steps (c) through (g), thereby removing substantially all radioactive sample from the gauze electrode and beaker in only two rinses.

In a preferred embodiment, stirring is done by means of a paddle-type stirring means and the process is carried out by means of an automated instrument.

In a further aspect of the present invention, in accordance with its objects and purposes, the apparatus of the invention comprises: (a) an aspirator tube having a first end and a second end; and (b) an automatable first positioning means (1) for inserting the first end of the aspirator tube to a single precise position so as to touch a gauze electrode at its bottom extremity and (2) for retracting the first end from its precise position during additions of liquid.

In a preferred embodiment, the gauze electrode is a controlled potential coulometry electrode and a paddle-type stirring means is used in cooperation with the apparatus described above, together with an automatable second positioning means for raising a liquid container to a level such that the bottom extremity of the gauze electrode contacts the bottom of the liquid container.

By the practice of the method of the invention, very thorough cleaning of a gauze electrode can be accomplished without movement of the aspiration tip, once it is placed into the precise position described above. Because the method is simple, it can readily be automated. Additionally, only a very small amount of rinse solution need be used; and thus only a very small volume of waste solution will be generated. Furthermore, only a short period of time need be used to do the cleaning. And because no spraying is used, splashing of the radioactive solutions will be minimized. Furthermore, by using the automated apparatus of the invention, besides the advantages listed above, very accurate readings have been obtained using the apparatus, due to the withdrawal of the aspiration tip. And when a non-magnetic stirrer (e.g., a paddle-type stirring means) is used, the accuracy further improves.

It is believed that both the method and apparatus of this invention are new, useful, and unobvious. The utility is stated above, and it is believed that the method and apparatus are new and unobvious for a variety of reasons. Regarding the apparatus, the approaches used in other automated instruments as described above are clearly different and they do not possess the advantages of the apparatus of the present invention, which themselves are evidence of unobviousness of the apparatus. Regarding the method, it is believed that it is new and unobvious. Others who have been faced with the problem of cleaning a gauze electrode, even manually, have not positioned an aspiration tip at the junction between the bottom of the electrolysis cell and the bottom of the gauze electrode. Instead, they have moved the aspiration tip to various parts of the gauze electrode while aspirating the liquid from the gauze.

BRIEF DESCRIPTION OF THE DRAWINGS

The accompanying drawings, which are incorporated in and form a part of the specification, illustrate an embodiment of the present invention and, together with the description, serve to explain the principles of the invention. In the drawings.

DESCRIPTION OF THE PREFERRED EMBODIMENTS

In all embodiments of the method of the invention, the tip of an aspirator tube must be precisely positioned so that it simultaneously touches both a gauze electrode at its bottom extremity and the bottom of a beaker which is used to contain material being analyzed. When the parts of the apparatus are thus positioned, it has been found that mere aspiration and two small rinses, as described below, has removed 99.9% of a plutonium sample which was present in the beaker for analysis. This extremely efficient cleaning of the gauze electrode (which is very difficult to clean) was accomplished without moving the aspirator tip, once it had been installed at the precise position described. The method can either be carried out manually or, preferably, can be automated as in the apparatus of the invention, as described below.

Figure 1:
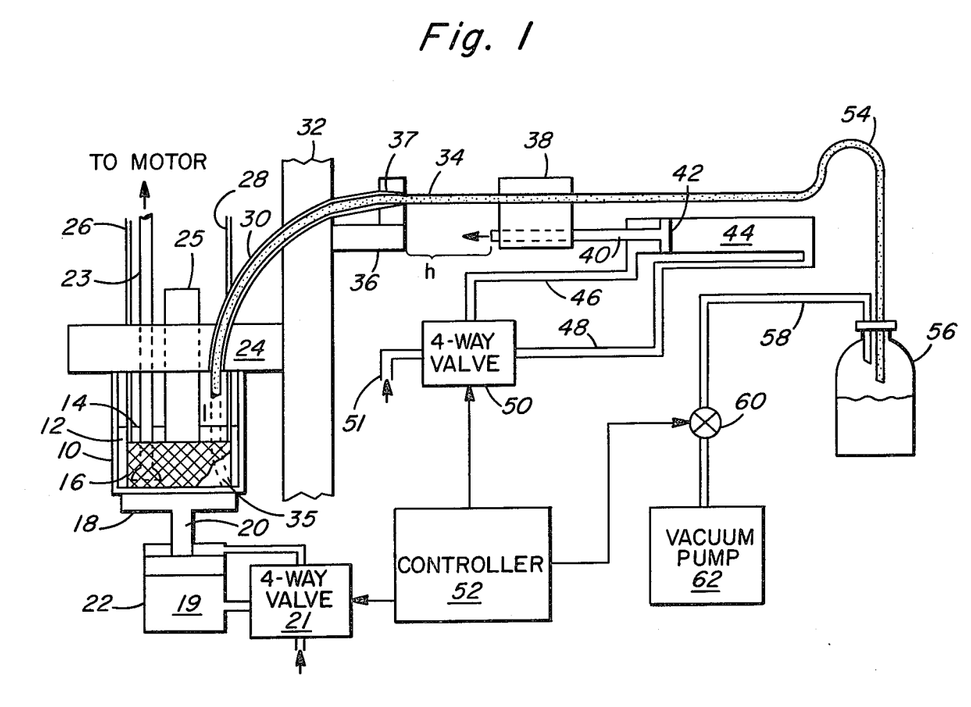
FIG. 1 is a diagrammatic illustration of an embodiment of the apparatus of the invention, showing particularly the electrolysis cell and its contents (drawn to scale) and other parts which are involved with the rinsing of the cell and its contents.

Referring to the drawing, in FIG. 1, an electrolysis cell 10 contains material to be analyzed 12, the top surface 14 of which preferably just covers the upper extremity of platinum gauze working electrode 16 (which is in the shape of a cylinder). The electrolysis cell 10 rests upon platform 18, which is connected by means of rod 20 to cell raising mechanism 22, (which is preferably a pneumatic cylinder 19 operated by a 4-way valve 21, through which compressed air is passed).

The platinum gauze electrode 16 is held in a fixed position with respect to a support 24 (made preferably of Teflon) by means of supports 26 and 28, which both support and act as enclosures for the electrical connections for platinum gauze working electrode 16. Supports 26 and 28 each pass through channels (not shown) in support 24. Support 24 also contains channels (not shown) through which pass stirring rod 23, counter electrode 25, and reference electrode 27 (not shown), the positions of which are described below in FIG. 2. Stirring rod 23 preferably has a paddle 29 at its bottom end.

Through a channel (not shown) in support 24, fixed outer guide tube 30 passes and is held in support 24 by interference fit. Outer guide tube 30 is also supported by support 32. Through outer guide tube 30 passes flexible tube 34. Tube 34 is shown in its retracted position in FIG. 1; the dotted lines 35 indicate the position of tube 34 when fluid is to be withdrawn. Tube 34 is inserted to the bottom of electrolysis cell 10 so that it touches both the bottom of the gauze electrode and the bottom of electrolysis cell 10 simultaneously when fluid is to be removed; and tube 34 is retracted so that its lower end is above upper surface 14 when fluid is not being removed.

Support 32, which is attached in a fixed position to lower guide tube support 24, has a channel located therein (not shown) which houses a portion of outer guide tube 30, through which flexible aspirator tube 34 passes. Support 32 is connected to upper guide tube support 36, which also has a channel located therein, through which a portion 37 of outer guide tube 30 passes. Portion 37 is narrowed as shown in order to achieve a gas-tight seal. Support block 36 also acts as a stop for connecting block 38, which is rigidly attached to rod 40 (which is attached to the movable piston 42 in pneumatic cylinder 44). Flexible aspirator tube 34 is fixed by means of screws (not shown) to connecting block 38. Thus, connecting block 38 forms a connector which rigidly connects tube 34 and rod 40. Pneumatic cylinder 44 has an orifice near each end thereof; and gas conduits 46 and 48 connect these orifices with four-way valve 50. Four-way valve 50 is connected at its third position to a compressed air inlet 51, and at its fourth position it is open to the atmosphere. The operation of four-way valve 50 is automated by means of controller 52.

Aspirator tube 34 has a curve 54, which allows for movement of tube 34, as described below. Aspirator tube 34 is connected to waste vessel 56, into which aspirated waste rinse solution is deposited. Also connected to waste vessel 56 is tube 58 which terminates at valve 60 (an on-off valve). Valve 60 in its open position is open to vacuum pump 62; and in its closed position is off. Valve 60 is operated by controller 52.

Cell raising mechanism 22 is preferably a pneumatic cylinder, which also can be operated by means of a four-way valve with attached conduits and using controller 52, as was described above for pneumatic cylinder 44.

Figure 2:
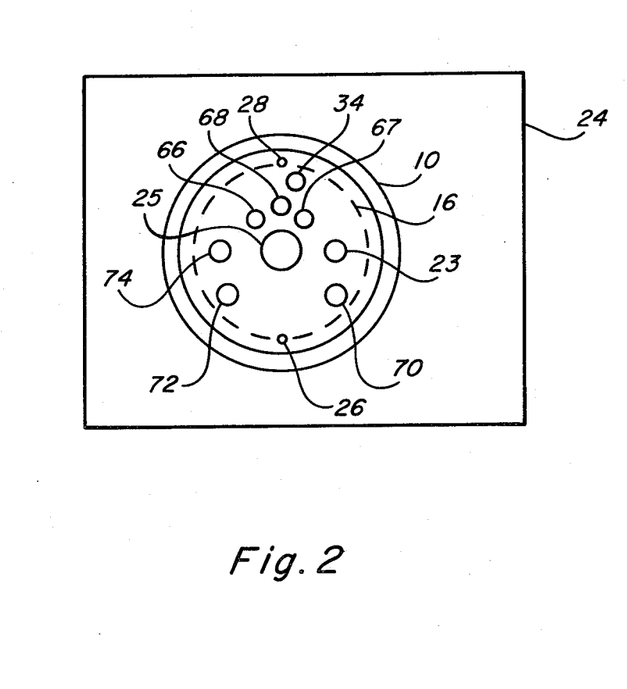
FIG. 2 is a cross-sectional view of the components of an embodiment of the apparatus which are supported above and extend down into the electrolysis cell.

In FIG. 2, a cross-sectional view is shown of a section taken horizontally through support 24 (shown in FIG. 1) showing the items which all pass through and are supported by support 24. Some, but not all, of these items were shown in FIG. 1. FIG. 2 is drawn to scale. Items which were shown in FIG. 1 are numbered as they were numbered in FIG. 1. Cell 10 forms the outer circular boundary in FIG. 2. Next is platinum gauze working electrode 16, which is supported by supports 26 and 28. Stirring rod 23 is also shown, as well as flexible tube 34 and counter electrode 25. All of the above-recited items were shown in FIG. 1. Additional items which for clarity were not shown in FIG. 1 include rinse solution dispenser 66, electrolyte dispenser 67, phosphate dispenser 68, inert gas inlet 70, inert gas outlet 72, and reference electrode 74.

The requirements of the positioning of the above-described elements are that the counter electrode 25 must be placed at the center of the cell 10, the platinum gauze working electrode 16 must be placed so that its center is located at the center of the cell, and the reference electrode 74 must be placed near the platinum gauze working electrode.

The operation of the rinsing apparatus shown in FIGS. 1 and 2 is as follows. Sample 12 is analyzed with tube 34 in its retracted position, with connecting block 38 in its farthest position from support 36 (at a distance h, which also corresponds to the distance from the end of tube 34 in its retracted position to the bottom of tube 34 when it is in its lowest position). In the retracted position of tube 34, compressed air from inlet conduit 51 passes into four-way valve 50 and out via conduit 46.

The cleaning sequence is as follows. The aspirator tube is lowered to its lowest position and the solution is removed by aspiration. This procedure is accomplished automatically by controller 52 actuating four-way valve 50 so that compressed air which enters four-way valve 50 via inlet conduit 51 leaves four-way valve 50 via conduit 48, thus forcing piston 42, rod 40, connecting block 38, and tube 34 to the left as shown in FIG. 1. These parts move to the left (in FIG. 1) until connecting block 38 is stopped by support 36, at which time the bottom end of flexible tube 34 contacts the bottom of platinum gauze working electrode 16 and the bottom of electrolysis cell 10. Controller 52 then actuates valve 60 so that it is in its open position and so that solution is aspirated out of cell 10 via flexible tube 34. This waste solution is deposited into waste vessel 56. Next, some small amount of rinse solution is added automatically into cell 10 by way of tube 66 (shown in FIG. 2) while aspirating. Next, tube 34 is withdrawn, as described above. Next, rinse solution is added to cell 10 via tube 66 to the height of the maximum sample volume which had been analyzed. Next, the solution is thoroughly stirred and then the aspirator tube is reinserted to its lowest position; and the rinse solution is aspirated until no visible liquid remains. Next, the aspirator tube 34 is retracted, as described above. Next, a slightly greater volume of rinse solution is added, the solution stirred, the aspirator tube 34 reinserted, and the rinse solution aspirated, as described above. Finally aspirator tube 34 is retracted.

In the cleaning sequence described above, it is required that the top surface 14 of solution always be lower than the tip of aspirator tube 34 when the tube is in its retracted position. Additionally, it is required that when aspiration is to be done, the lower end of tube 34 be precisely positioned at the junction between the bottom of cell 10 and the bottom of platinum gauze working electrode 16. Thus, it is very important that platform 18 be accurately positioned so that tube 34 can aspirate when it is located in the precise position described above.

Figure 3:
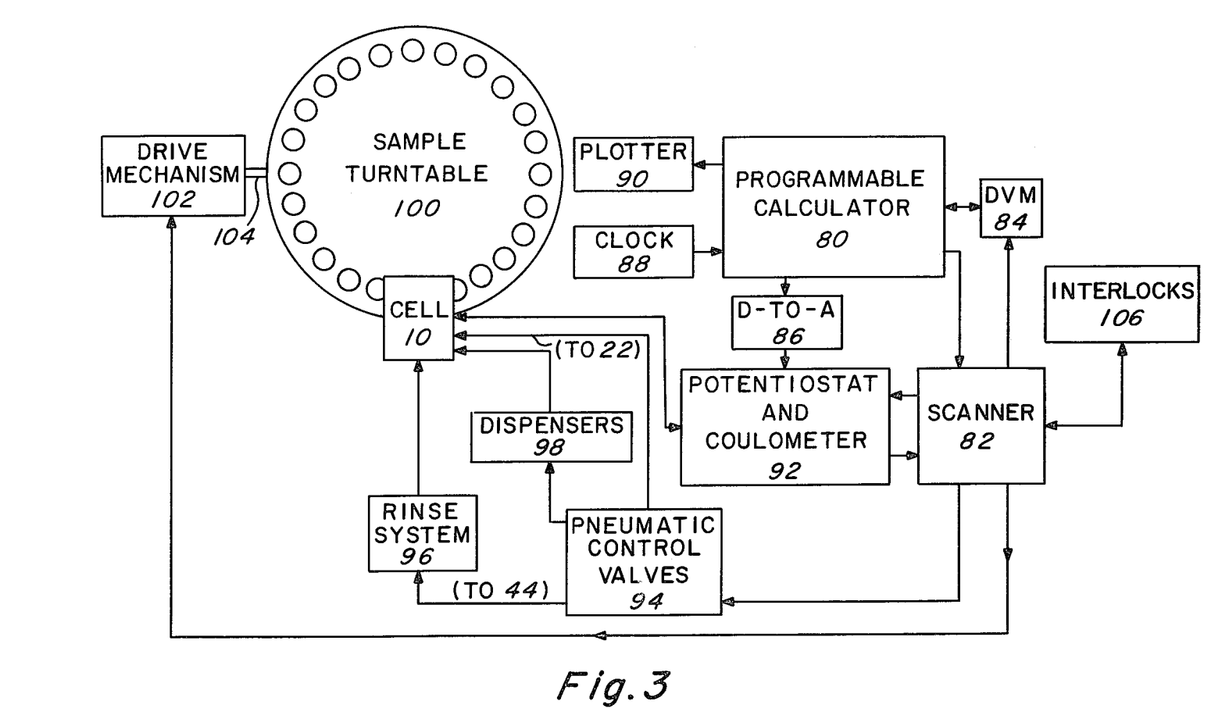
FIG. 3 is a block diagram, showing the electrolysis cell and other apparatus shown in FIG. 1, as well as electronic apparatus suitable for automating the rinsing apparatus. Electronic connections are illustrated by lines, the arrows indicating direction of flow of signal or of data paths.
Figure 4:
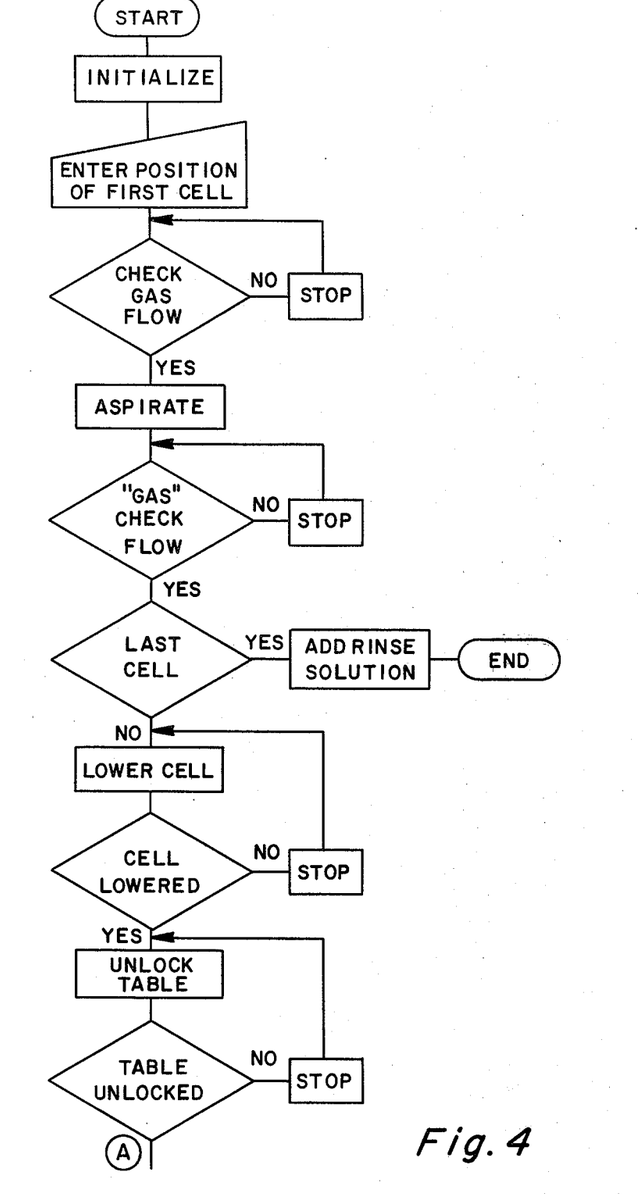
FIGS. 4–9 are a flow diagram suitable for automatically operating the apparatus of FIGS. 1, 2, and 3.
Figure 5:
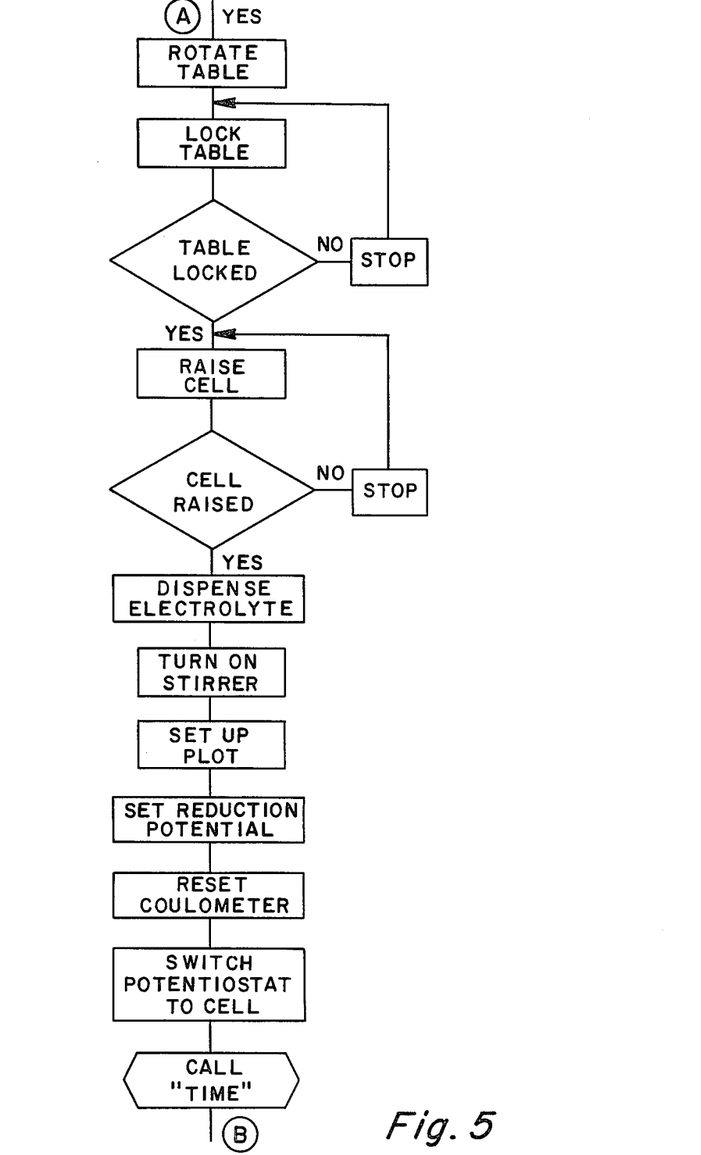
Figure 6:
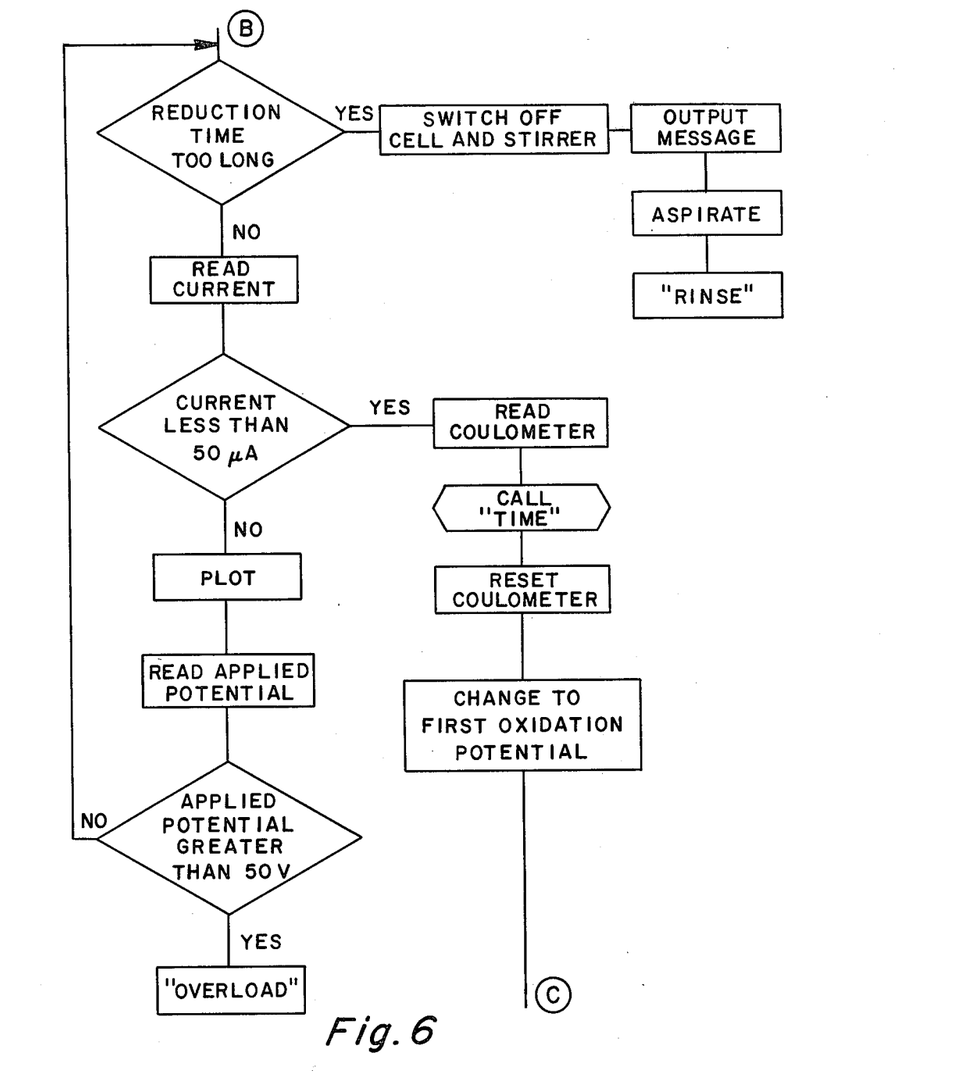
Figure 7:
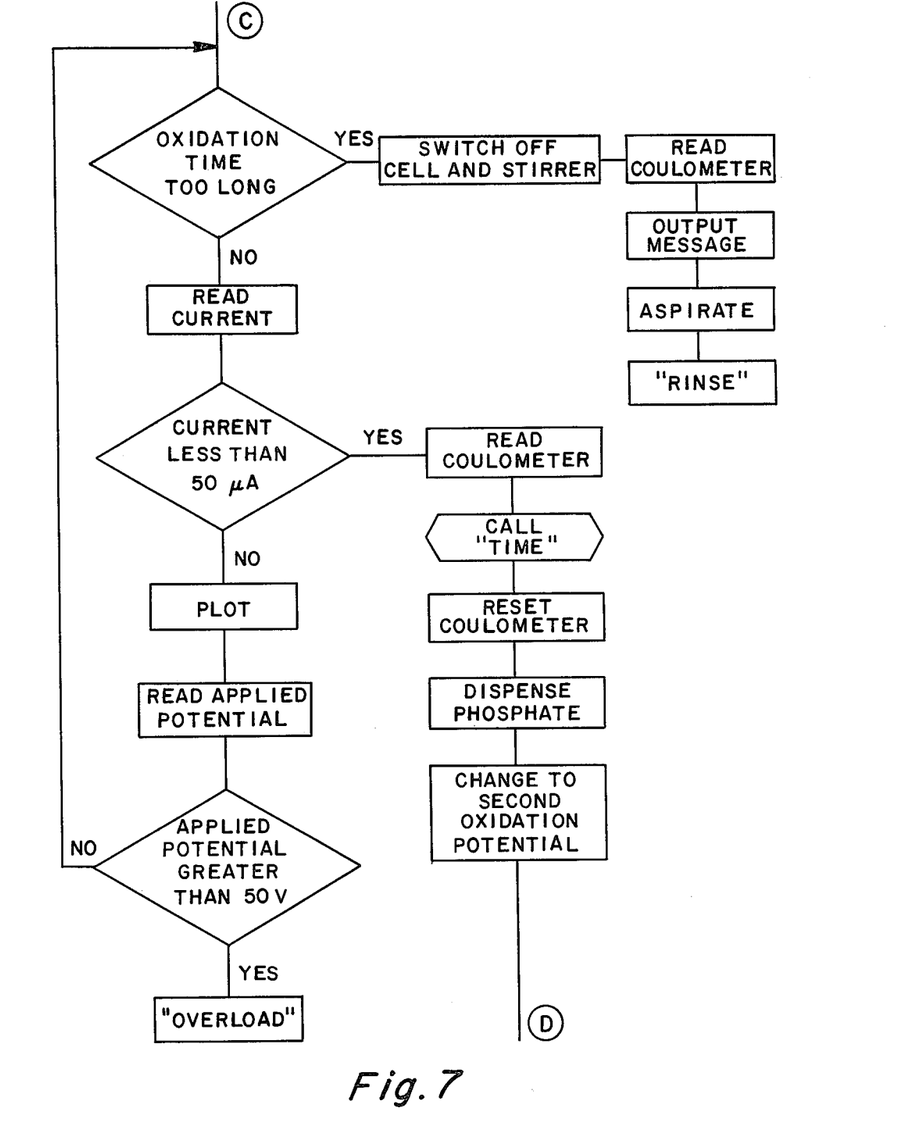
Figure 8:
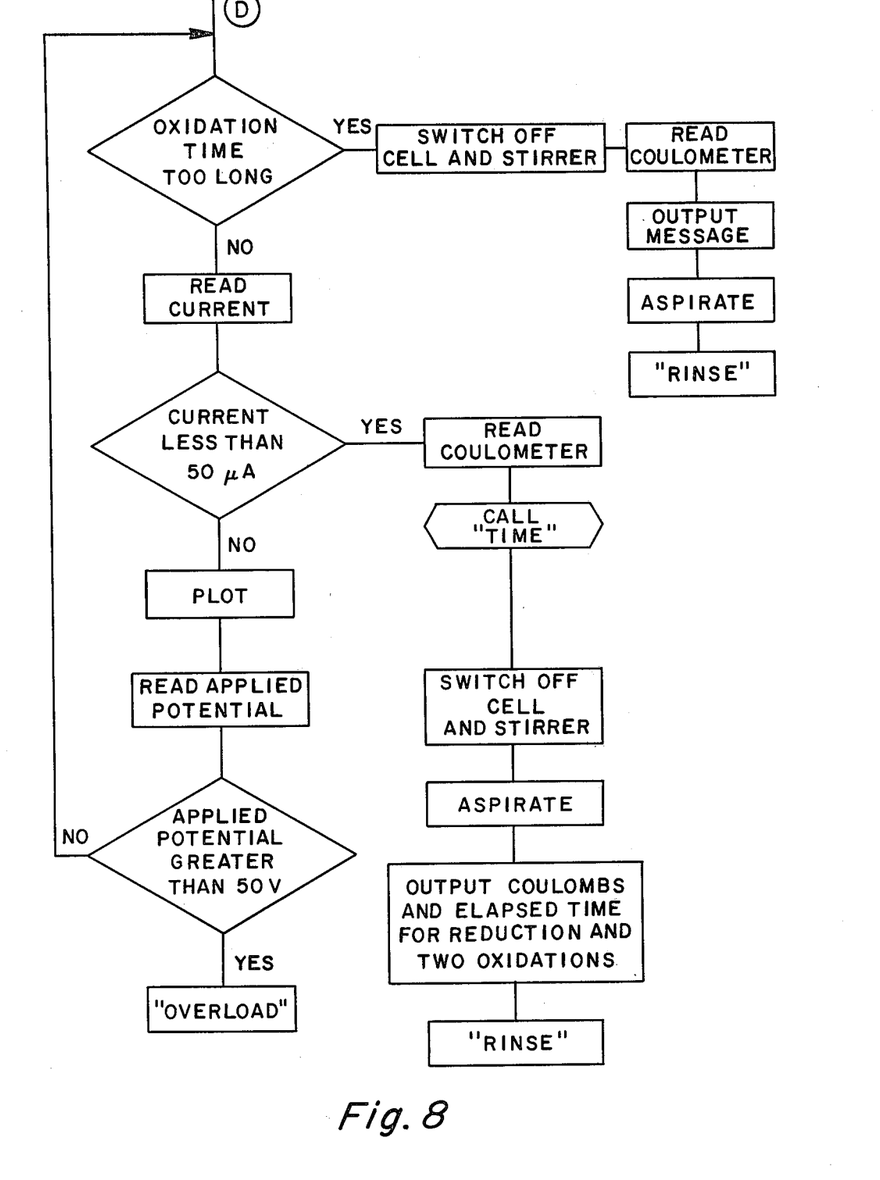
Figure 9:
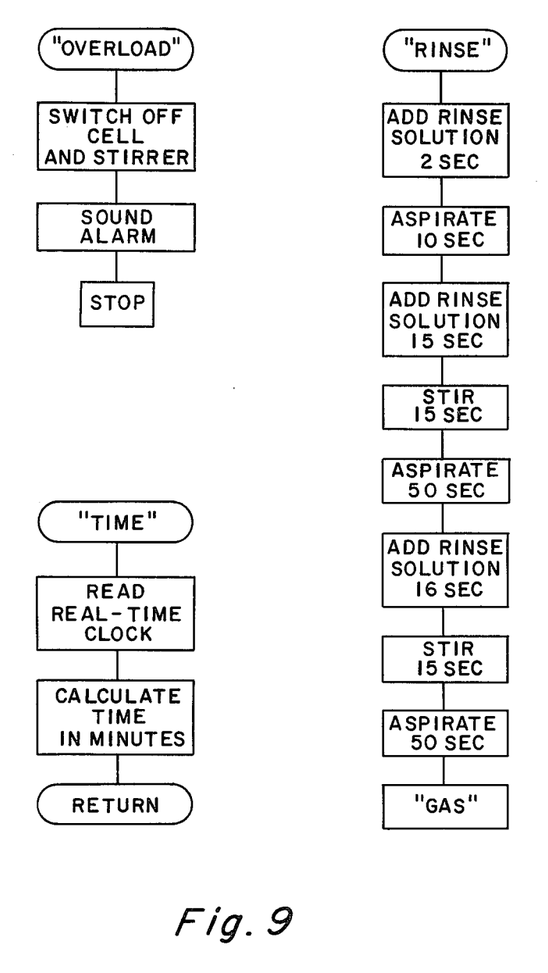

In FIG. 3 a schematic diagram is shown, illustrating the electronic parts and their cooperation with the mechanical parts of an embodiment of apparatus in which the rinsing and cleaning system of the invention is especially useful.

In FIG. 3, programmable calculator 80 and scanner 82 (together with a solenoid valve not shown) make up controller 52 (which was shown in FIG. 1). Interfaced with and under control of the calculator 80 are scanner 82, digital voltmeter 84, a digital-to-analog converter 86, a clock 88 and a digital plotter 90 as shown in FIG. 3. The calculator controls most functions of the potentiostat and coulometer 92, and it receives and processes data from them. Scanner 82 sends a signal to pneumatic control valves 94 (which include valve 60, four-way valve 50, four-way valve 21, and solenoid valves not shown). Pneumatic control valves 94 control rinse system 96 (which includes pneumatic cylinder 44, waste vessel 56, movable cylinder 38, and flexible aspirator tube 34, all of which are shown in FIG. 1). Pneumatic control valves 94 also control dispensers 98 (shown in detail in FIG. 2) and cell raising mechanism 22 (shown in FIGS. 1 and 3). Sample turntable 100 is operated by drive mechanism 102. Rigid rod 104 connects turntable 100 and drive mechanism 102. Drive mechanism 102 is operated by scanner 82. Scanner 82 also controls the motor (not shown) which operates stirring rod 23. A system of interlocks 106 operates in cooperation with scanner 82, turning off the apparatus upon receipt of certain signals from scanner 82.

In FIGS. 4–9, a flow diagram suitable for operating the automated instrument shown in FIGS. 1, 2, and 3 is summarized. This operation is particularly useful for carrying out automatically a plutonium determination using the controlled potential coulometric method which was fully described in D. D. Jackson et al., "Controlled-Potential Coulometric Determination of Plutonium with a Hydrochloric Acid-Sulfamic Acid Electrolyte and Phosphate Complexing," *Analytica Chimica Acta*, 117 (1980) 205–215; and that article is hereby incorporated herein by reference.

The method features high specificity, a precision of 0.1 to 0.2% relative standard deviation at the 5-mg plutonium level, and operational simplicity for adaptation to an automated instrument. Plutonium is reduced to Pu(III) in HCl-sulfamic acid electrolyte, diverse ions are oxidized at a potential below that at which Pu(III) is significantly oxidized, phosphate is added to lower the Pu(III)-Pu(IV) potential, and Pu(III) is titrimetrically oxidized to Pu(IV).

All operations of the apparatus shown in FIG. 3 are automated, including sample transport, reagent deliveries, the reduction and two oxidation electrolyses, data computation with output on paper tape and a display of the electrolyses, and cleaning of cells, stirrer, and electrodes. The analyst delivers weight or volume portions of samples, normally containing 5 milligrams of plutonium in a volume up to two milliliters into cells 10, places them in the turntable, and initiates the automated operation. The programmable calculator 80 controls all mechanical and electrical operations, and it processes data.

The control system (the parts of which are shown in FIG. 3, including the programmable calculator 80, clock 88, digital voltmeter 84, scanner 82, digital-to-analog converter 86, potentiostat and coulometer 92, and plotter 90) are connected together as shown in FIG. 3; and their operation and details and requirements of their construction are fully described in D. D. Jackson and S. F. Marsh, "LASL Analytical Chemistry Program for Fissionable Materials Safeguards," National Bureau of Standards Special Publication 582, "Measurement Technology for Safeguards and Materials Control," U.S. Department of Commerce, NBS, issued June, 1980, pp. 129–139. That report is hereby incorporated herein by reference.

Interlocks 106 are incorporated into the apparatus at various places, including that shown in FIG. 3. They minimize the possibility of instrument damage or a faulty analysis. Indications of possible damage to the instrument terminate operation; however, if only the analysis is affected, the automated operation stops the analysis of that sample and then continues with the next sample.

The dispensed volumes of the electrolyte and phosphate solutions are adjusted by mechanical stop positions on hydraulic cylinder mechanisms. Just enough electrolyte is added to cover platinum gauze working electrode 16. The phosphate solution is dispensed to provide a 1 M phosphate concentration in the cell solution, calculated disregarding sample volume. Volumes of rinse solution are controlled by programming the elapsed time of pump operation.

To avoid splashing, the delivery tips of phosphate dispenser 68, rinse solution dispenser 66, and electrolyte dispenser 67 dispense all solutions onto the electrolysis bridge tube of the counter electrode. The tips are cut at 45° and are bent slightly toward the bridge tube.

Premature delivery of the phosphate solution is prevented by separating the tips of the three dispensers (shown in FIG. 2) by a small distance (e.g., 1 mm.). The tip of the electrolyte dispenser 67 is lowest, the tip of the phosphate dispenser 68 is next, and the tip of the rinse solution dispenser 66 is on top, so that any adhering electrolyte and phosphate solutions are removed during the rinse operation. Delivery rates of the electrolyte and phosphate solution dispensers are adjusted by needle valves (not shown) located downstream for pneumatic control valves 94 to provide smooth motions of the syringe plungers (which deliver reagents) and steady-rate deliveries without splashing. The delivery rate of the rinse solution dispenser 66 is adjusted to 2 milliliters per second. The position of each of these 3 dispensers relative to each other and the relative distance that each extends down into the cell are important variables. Complete details of the dispensing system, including drawings, are in D. D. Jackson, et al., "Automated Spectrophotometer for Plutonium and Uranium Determination," Los Alamos Report LA-6901, UC-15, issued February, 1976, especially on page 7 (general description), page 13 (adjustment), and page 29 (construction details); and that report is hereby incorporated herein by reference.

The sample transport system (including the operation of sample turntable 100, drive mechanism 102, rod 104, and cell raising mechanism 22, as well as their relationship to scanner 82 and programmable calculator 80) are described in detail in LA-6091 (February, 1976) cited above at page 23; and that report has been incorporated herein by reference.

The turntable (shown in FIG. 3) holds up to 24 electrolysis cells 10 that rotate to the measurement station (i.e., support 24). The turntable is rotated by a Geneva-drive intermittent-motion assembly that provides slow acceleration and accurate positioning. Positional accuracy is further ensured by the mechanism of cylindrical rod 104, driven by a pneumatic cylinder, that engages slots in the edge of the turntable 100 at each of the 24 positions.

Basic details of the electrolysis cell, (including drawings and discussion) are fully described in the *Anal. Chim. Acta* article cited above (especially on page 208); and that reference has been incorporated herein by reference.

The angle which is drilled into Teflon support 24 and which is suitable for the rinsing apparatus of the present invention will be selected depending upon the flexibility of tubing 34 which is chosen to be used in the apparatus. When the tubing is lowered to the cell bottom, however, the tip of the tubing must touch the gauze electrode.

EXAMPLE

An automated apparatus was constructed which had the parts and configuration as shown in FIGS. 1, 2, and 3. The flow chart shown in FIGS. 4–9 was used to program programmable calculator 80.

Electrolysis cells were fabricated from glass tubing of 4.8 cm diameter and 0.2 cm wall thickness. Each cell 10 had a height of 4.5 cm with ±0.05 cm tolerance to prevent damage to the working electrode 16 and to attain effective aspiration of solution. Each cell bottom was flat, thus avoiding interference with the paddle of stirring rod 23 and leading to effective aspiration. Each cell top was ground flat and fire-polished lightly to produce a gas-tight seal with support 24 (which was made of Teflon). The platinum gauze working electrode 16 was made by folding 45-mesh platinum gauze so as to provide a three-layer structure having loose ends at its top and bottom. The loose end at the top was fused to the gauze and to a 1.5 mm. platinum wire at a multiplicity of points. The loose end at the bottom was not fused and was located within the folds of the gauze. This structure was then formed into the shape of a cylinder and was fused closed at a multiplicity of points. The top of the closure was also fused to a 14-gauge platinum wire 26 at one point; and another 14-gauge platinum wire 28 was fused at the top. The positions of supports 26 and 28 are shown in FIG. 2. The cylinder had a height of 15 mm. and an outer diameter of 40 mm.

The counter electrode was 18-gauge platinum wire having one end folded for increased surface area.

The reference electrode was a Beckman Model 392-70 saturated-calomel electrode.

Commercially available bridge tubes having porous Vycor frits, purchased from Princeton Applied Research, were used for both the counter and reference electrodes. The bridge tube for the counter electrode was Model 9615; and that for the reference electrode was 9616. The Vycor frits provided high electrical conductivity at very low flow rates of electrolyte and were attached with heat-shrinkable Teflon tubing. The tip of the reference bridge tube was located adjacent to the working electrode 16 for best control of the working electrode potential. The counter electrode 25 was located in the geometric center of the working electrode 16 to attain a uniform potential gradient.

A paddle-type stirring means was used and was driven by an 1800-rpm synchronous motor which was rigidly mounted above Teflon support 24. A 0.5-cm diameter glass rod was heated and flattened at one end to produce a paddle which was about 1.2 cm wide, 0.6 cm high, and 0.3 cm thick. The Teflon support 24 provided a low-friction bearing surface preventing wobble. The stirring rod 23 was connected to the motor spindle by a flexible coupling of rubber tubing.

The type of tubing which was used to form aspirator tube 34 was made of Teflon and had an inner diameter of 1.6 mm. and an outer diameter slightly smaller than 3.2 mm. Outer guide tube 30 was also made of Teflon tubing which had an inner diameter of 3.2 mm. and an outer diameter of 4.0 mm.; and it was held in a fixed position as shown in FIG. 1.

An angle of about 15° was drilled in support 24. This angle was chosen because of characteristics of the particular tubing 34 that was used. The distance h shown in the drawing was about 30 mm.; and the upper level of solution 14 above the bottom of cell 10 was never greater than about 25 mm.

Pneumatic cylinder 44 was a ⅜ inch bore, 2 inch stroke, double acting cylinder which was purchased from Clippard Instrument Lab., Inc. and had Model No. 3BDS-2 (and was shown on page 5 of catalog no. 272). Four-way control valves 21 and 50 were purchased from Clippard and had Model No. MJV-4 (and was shown on page 8 of catalog no. 172).

Vacuum pump 62 was a 1.8-cfm-diaphragm air pump operating at −0.6 atm.

Cell raising mechanism 22 used a pneumatic cylinder 19 which was double acting and had a ⅜ inch bore and a 3 inch stroke. It was purchased from Clippard Company and had Model No. 3 BDS-3 (shown on page 5 of catalog no. 272). Valve 60 was a two-way Teflon solenoid valve purchased from General Valve Company (Series 2, Model 1 in their General Valve Catalog).

Controller 52 (shown in FIG. 1) was made up of scanner 82 and programmable calculator 80 (both shown in FIG. 3) and a solenoid valve (not shown) which was purchased from Clippard Company (having Model No. AVSC-115, found on page 22 of catalog 172). The four-way valves 50 and 21 were each controlled by a solenoid, which was in turn actuated by scanner 82, which was in turn controlled by programmable calculator 80.

The phosphate dispenser 68, rinse solution dispenser 66, and electrolyte dispenser 67 were formed from small diameter Teflon tubing. They and the other components and their configurations (as shown in FIG. 2) correspond to those of the apparatus that was built. The positions of the three dispensers relative to each other were important. The tip of the electrolyte dispenser 67 was lowest, the tip of the phosphate dispenser 68 was next, and the tip of the rinse solution dispenser 66 was on top, so that any adhering electrolyte and phosphate solutions were removed during the rinse operation. The absolute height of these three dispensers was not critical; however, the dispenser tubes had to extend below the surface of support 24 and they all had to be short enough so that they did not extend at any time into the upper level of solution 14.

Also included in the constructed apparatus were the additional parts that are shown in FIG. 3. The parts and their connections were as shown in FIG. 3. The programmable calculator 80 was a Hewlett-Packard 9825A Programmable Calculator with 98210A String-Advanced Programming, 98216A Plotter General I/O-Extended I/O ROMs, and 98034A HPIB and 98033A BCD Interface Cards. Programs were written which carried out the flow diagram shown in FIGS. 4–9 in HPL, a high-level language. The sequence and timing of operations were controlled accurately by the calculator. Real-time decisions affecting the analysis were made and acted upon.

Full details of the construction of the remainder of the apparatus (excluding interlocks 106), including scanner 82, potentiostat and coulometer 92, D-to-A converter 86, DVM 84, clock 88, plotter 90, drive mechanism 102, and turntable 100 are given in the references described above which have been incorporated herein by reference, the particular pages cited above giving accurate descriptions of these parts of the instrument and their required relationships to each other.

The interlocks 106 are monitored by the calculator 80 through the DVM 84.

Using the automated instrument which was built as described above, plutonium samples were analyzed according to the method which was described in the *Anal. Chim. Acta* article cited above, which has been incorporated herein by reference.

Following each analysis, rinsing and cleaning of the electrolysis cell 10 and its contents, including the gauze electrode 16, were carried out according to the method of the invention as automated by the instrument described above. The aspirator tube 34 was inserted following an analysis and the cell contents were aspirated out with the aspirator tube tip positioned at the junction between the cell bottom and the bottom of the gauze electrode. A small amount (e.g. 4 ml) of rinse solution was added while aspirating, in order to remove any precipitate that may have been present. Then, the aspirator tube 34 was retracted, about 25 ml. of rinse solution was added through tube 66, and stirring was done. Then, the aspirator tube was reinserted and the rinse solution was aspirated. Next the aspirator tube was retracted and about 26 ml. of rinse solution was added, and the solution was stirred. The aspirator tube was reinserted and aspiration was done.

Using the method and automated apparatus of the invention, 99.98% of the plutonium which has been present in the cell was removed by using only about 80 ml. of rinse solution and less than 3 minutes of time. The amount remaining was determined at the completion of rinsing by adding more acid and stirring (for about 5 minutes) and then counting the emitted $\alpha$-particles in a scintillation counter.

The foregoing description of preferred embodiments of the invention has been presented for purposes of illustration and description. It is not intended to be exhaustive or to limit the invention to the precise forms disclosed, and obviously many modifications and variations are possible in light of the above teaching. The embodiments were chosen and described in order to best explain the principles of the invention and their practical application to thereby enable others skilled in the art to best utilize the invention in various embodiments and with various modifications as are suited to the particular use contemplated. It is intended that the scope of the invention be defined by the claims appended hereto.

What is claimed is:

1. An apparatus for cleaning by suction with the aid of capillary action and gravity a structure to be cleaned which is located within a container for containing liquid, comprising in combination:
   (a) a flexible tube having a first end and a second end wherein a suction means is to be operably connected to said second end; and
   (b) an automatable first positioning means
      (1) for inserting said first end of said tube to a precise position so that said first end simultaneously touches (i) the structure to be cleaned at its bottom extremity and (ii) the bottom of the container and removes by suction with the aid of capillary action and gravity substantially all liquid located on the structure to be cleaned and substantially all other liquid located within the liquid container, and
      (2) for holding said first end at said precise position during suctioning.

2. An apparatus according to claim 1, wherein said structure to be cleaned comprises a gauze electrode and wherein said automatable first positioning means also retracts said first end from said precise position to a position above liquid level during additions of wash liquid to the container.

3. An apparatus according to claim 2, wherein said gauze electrode is a controlled potential coulometry working electrode, wherein said automatable first positioning means comprises a pneumatic cylinder, and wherein said apparatus includes also a tube for adding wash liquid to the container without splashing or spraying.

4. An apparatus for chemically analyzing liquid samples and for self-cleaning between measurements, comprising an apparatus according to claim 3, and including also in combination therewith (a) the structure to be cleaned comprising a gauze electrode which said tip touches simultaneously when it touches the bottom of said liquid container,
(b) a reference potential electrode, and (c) a counter potential electrode, all three of which elements are stationarily and continuously positioned within said liquid container and operable in cooperation with electrical activating apparatus so as to provide an apparatus for chemically analyzing liquid samples located within the liquid container.

5. An apparatus according to claim 4, and including also located within the container
   (a) a paddle-type stirring means for stirring liquid located within the liquid container and (b) a support means for supporting said paddle-type stirring means in a position so that stirring can occur, wherein said paddle-type stirring means, said reference potential electrode, and said counter potential electrode are spaced only far enough apart within the container to permit stirring movement of said stirring means, thus permitting use of a liquid container having a diameter substantially equal to the diameter of said gauze electrode and thus aiding in minimizing the amount of liquid needed to clean the container, the gauze electrode, and all other contents of the container.

6. An apparatus according to claim 4 or claim 5 and including also an automatable second positioning means for lowering and raising said liquid container to a height such that the bottom of said gauze electrode touches the bottom of said liquid container.

7. An apparatus according to claim 6, wherein said automatable second positioning means comprises a pneumatic cylinder.

8. An apparatus according to claim 7, wherein said gauze electrode has a cylindrical shape and is open at its top and bottom and wherein said apparatus comprises also in operable communication therewith a controller for controlling an automating said first positioning means, said second positioning means, and said stirring means.

9. Apparatus for very thoroughly cleaning a container and a gauze electrode located within and at the bottom of the container, using only a small amount of wash liquid, said apparatus comprising in operable communication:
   (a) means for withdrawing an analysis solution from the container and from the gauze electrode, said means for withdrawing comprising a flexible tune having a tip which is positionable at a precise position at the junction of the lowest extremity of the gauze electrode and the bottom of the container;
   (b) means for positioning and holding said tip at said precise position;
   (c) means for retracting said tip from said precise position during additions of wash liquid to the container;
   (d) a tube for adding wash liquid to the container while the gauze electrode remains at its stationary position on the bottom of the container;
   (e) means for stirring said wash liquid in the presence of the gauze electrode;
   (f) means for reinserting said tip to said precise position;
   (g) means for aspirating said wash liquid while said tip is located at said precise position, thus removing all visible liquid from the bottom of the container and from the gauze electrode.

* * * * *